United States Patent
Tuitupou et al.

(10) Patent No.: US 8,480,638 B2
(45) Date of Patent: Jul. 9, 2013

(54) INTRAOCULAR IONTOPHORETIC DEVICE AND ASSOCIATED METHODS

(75) Inventors: Anthony L. Tuitupou, Salt Lake City, UT (US); John W. Higuchi, Salt Lake City, UT (US)

(73) Assignee: Aciont, Inc., Salt Lake City, UT (US)

( * ) Notice: Subject to any disclaimer, the term of this patent is extended or adjusted under 35 U.S.C. 154(b) by 527 days.

(21) Appl. No.: 11/867,503

(22) Filed: Oct. 4, 2007

(65) Prior Publication Data
US 2009/0093780 A1 Apr. 9, 2009

(51) Int. Cl.
*A61M 35/00* (2006.01)

(52) U.S. Cl.
USPC ............ 604/294; 604/300; 604/521; 604/501

(58) Field of Classification Search
USPC .................. 604/294, 300; 424/427; 514/789
See application file for complete search history.

(56) References Cited

U.S. PATENT DOCUMENTS

| | | | | |
|---|---|---|---|---|
| 2,525,381 A | * | 10/1950 | Tower | 604/20 |
| 3,710,796 A | * | 1/1973 | Neefe | 424/429 |
| 3,760,807 A | * | 9/1973 | Neefe | 424/429 |
| 3,786,812 A | * | 1/1974 | Neefe | 424/429 |
| 3,910,618 A | * | 10/1975 | Massenz | 294/1.2 |
| 3,916,899 A | * | 11/1975 | Theeuwes et al. | 424/424 |
| 3,957,049 A | * | 5/1976 | Neefe | 424/429 |
| 4,014,335 A | * | 3/1977 | Arnold | 424/427 |
| 4,109,648 A | * | 8/1978 | Larke et al. | 600/383 |
| 4,240,163 A | * | 12/1980 | Galin | 623/6.57 |
| 4,564,016 A | * | 1/1986 | Maurice et al. | 604/20 |
| 4,592,752 A | * | 6/1986 | Neefe | 424/429 |
| 4,709,996 A | * | 12/1987 | Michelson | 359/665 |
| 5,098,443 A | * | 3/1992 | Parel et al. | 128/898 |
| 5,201,764 A | * | 4/1993 | Kelman et al. | 623/6.59 |
| 5,270,051 A | * | 12/1993 | Harris | 424/427 |
| 5,292,514 A | * | 3/1994 | Capecchi et al. | 424/422 |
| 5,376,116 A | * | 12/1994 | Poler | 623/6.16 |
| 5,401,508 A | * | 3/1995 | Manesis | 424/427 |
| 5,433,714 A | * | 7/1995 | Bloomberg | 604/289 |
| 5,472,436 A | * | 12/1995 | Fremstad | 604/294 |
| 5,554,187 A | * | 9/1996 | Rizzo, III | 623/6.16 |
| 5,593,438 A | * | 1/1997 | Akhavi et al. | 623/6.16 |
| 5,830,173 A | * | 11/1998 | Avery et al. | 604/9 |
| 6,154,671 A | * | 11/2000 | Parel et al. | 604/20 |
| 6,319,240 B1 | * | 11/2001 | Beck | 604/501 |
| 6,539,251 B2 | * | 3/2003 | Beck et al. | 604/20 |

(Continued)

OTHER PUBLICATIONS

Scleral lens—Wikipedia, the free encyclopedia. http://en.wikipedia.org/wiki/Scleral_lens. As accessed on Jun. 8, 2007. 2 pages.

(Continued)

*Primary Examiner* — Susan Su (74) *Attorney, Agent, or Firm* — Thorpe North & Western LLP (57) ABSTRACT

The present invention includes methods and devices for non-invasively delivering an active agent to the eye of a subject. In one aspect, for example, a device for delivering an active agent to an eye of a subject may include an ocular lens-shaped housing configured to contact a surface of the eye, and a reservoir coupled to the housing and configured to deliver an active agent to the eye, wherein the reservoir is located entirely within a 180 degree section of the housing. In another aspect, the reservoir is located entirely within a 150 degree section of the housing.

14 Claims, 4 Drawing Sheets

U.S. PATENT DOCUMENTS

| | | | |
|---|---|---|---|
| 6,728,573 B1* | 4/2004 | Beck et al. | 604/20 |
| 6,953,446 B2* | 10/2005 | Fischer | 604/93.01 |
| 7,151,960 B1* | 12/2006 | Newsome | 604/20 |
| 7,164,943 B2* | 1/2007 | Roy | 604/20 |
| 7,195,774 B2* | 3/2007 | Carvalho et al. | 424/427 |
| 7,346,389 B1* | 3/2008 | Newsome | 604/20 |
| 2002/0016575 A1* | 2/2002 | Beck et al. | 604/294 |
| 2002/0035345 A1* | 3/2002 | Beck | 604/20 |
| 2003/0035083 A1* | 2/2003 | Francis et al. | 351/162 |
| 2003/0065293 A1* | 4/2003 | Hess | 604/294 |
| 2004/0096477 A1* | 5/2004 | Chauhan et al. | 424/429 |
| 2004/0241207 A1* | 12/2004 | Chauhan et al. | 424/429 |
| 2006/0089590 A1* | 4/2006 | Higuchi et al. | 604/20 |
| 2007/0106278 A1* | 5/2007 | Higuchi et al. | 604/891.1 |
| 2007/0112295 A1* | 5/2007 | Roy | 604/20 |
| 2007/0112318 A1* | 5/2007 | Leahy et al. | 604/294 |
| 2007/0123814 A1* | 5/2007 | Roy | 604/20 |
| 2007/0299386 A1* | 12/2007 | Peyman | 604/20 |
| 2008/0039769 A1* | 2/2008 | Peyman | 604/20 |
| 2008/0107713 A1* | 5/2008 | Orilla et al. | 424/429 |
| 2008/0286338 A1* | 11/2008 | Rosenthal et al. | 424/427 |
| 2009/0004244 A1* | 1/2009 | Orilla et al. | 424/429 |
| 2009/0004245 A1* | 1/2009 | Orilla et al. | 424/429 |

OTHER PUBLICATIONS

GELFLEX Laboratories, Gas Permeable Scleral. http://www.gelflex.com/pages/gas_schleral.asp. As accessed on Jun. 8, 2007. 2 pages.

U.S. Appl. No. 12/903,837; filed Oct. 13, 2010; Anthony L. Tuitupou; office action dated Sep. 13, 2012.

* cited by examiner

INTRAOCULAR IONTOPHORETIC DEVICE AND ASSOCIATED METHODS

FIELD OF THE INVENTION

The present invention relates to systems, methods, and devices for the ocular delivery of an active agent into a subject's eye. Accordingly, the present invention involves the fields of chemistry, pharmaceutical sciences, and medicine, particularly ophthalmology.

BACKGROUND OF THE INVENTION

Posterior and intermediate eye diseases that require ocular drug delivery to prevent blindness include uveitis, bacterial and fungal endophthalmitis, age-related macular degeneration, viral retinitis, and diabetic retinopathy, among others. For example, the reported incidence of posterior uveitis is more than 100,000 people in the United States. If left untreated, uveitis leads to blindness. It is responsible for about 10 percent of all visual impairment in the U.S. and is the third leading cause of blindness worldwide.

Treatments of intermediate and posterior uveitis are complicated by the inaccessibility of the posterior eye to topically applied medications. Current therapy for intermediate and posterior uveitis requires repeated periocular injections and/or high-dose systemic therapy with corticosteroids. Injections are usually preferred to systemic drug administration because the blood/retinal barrier impedes the passage of most drugs from the systemically circulating blood to the interior of the eye. Additionally, large systemic doses are needed to treat intermediate and posterior uveitis, which often result in systemic toxicities including immunosuppression, adrenal suppression, ulcerogenesis, fluid and electrolyte imbalances, fat redistribution and psychological disorders.

Endophthalmitis affects approximately 10,000 people in the United States each year. Endophthalmitis is typically caused by gram-positive bacteria after ocular surgery or trauma, but it can also be fungal or viral in nature. The current method of treating endophthalmitis is direct injection of antimicrobials into the vitreous. Intravitreal injections are necessary because periocular injections and systemic administration do not deliver efficacious amounts of antibiotics to the target sites in the eye.

Treatments of posterior eye diseases require intravitreal and periocular injections or systemic drug administration. Systemic administration is usually not preferred because of the resulting systemic toxicity as discussed above. While intravitreal and periocular injections are preferable to systemic administration, the half-life of most injected compounds in the vitreous is relatively short, usually on the scale of just a few hours. Therefore, intravitreal injections require frequent administration. The repeated injections can cause pain, discomfort, intraocular pressure increases, intraocular bleeding, increased chances for infection, and the possibility of retinal detachment. The major complication of periocular injections is accidental perforation of the globe, which causes pain, retinal detachment, ocular hypertension, and intraocular hemorrhage. Other possible complications of periocular injections include pain, central retinal artery/vein occlusion, and intraocular pressure increases. Therefore, these methods of ocular drug delivery into the posterior of the eye have significant limitations and major drawbacks. In addition, injections are very poorly accepted by patients. These methods also involve high healthcare cost due to the involvement of skilled and experienced physicians to perform the injections.

Ocular iontophoresis is a noninvasive technique used to deliver compounds of interest into the interior of a patient's eye. In practice, two iontophoretic electrodes are used in order to complete an electrical circuit. In traditional, transscleral iontophoresis, at least one of the electrodes is considered to be an active iontophoretic electrode, while the other may be considered as a return, inactive, or indifferent electrode. The active electrode is typically placed on an eye surface, and the return electrode is typically placed remote from the eye, for example on the earlobe. The compound of interest is transported at the active electrode across the tissue when a current is applied to the electrodes. Compound transport may occur as a result of a direct electrical field effect (e.g., electrophoresis), an indirect electrical field effect (e.g., electroosmosis), electrically induced pore or transport pathway formation (electroporation), or a combination of any of the foregoing. Examples of currently known iontophoretic devices and methods for ocular drug delivery may be found in U.S. Pat. Nos. 6,319,240; 6,539,251; 6,579,276; 6,697,668, and PCT Publication Nos. WO 03/030989 and WO 03/043689, each of which is incorporated herein by reference.

One potential problem with present ocular iontophoretic methods and devices concerns the actual delivery, or rather, the non-delivery of the drug into the eye tissue. Because the return electrode is located remote from the eye, various conductive pathways may be formed. Such divergence of the electric current will decrease the efficiency of drug delivery to the target sites in the eye, and as a result, much of the drug may be delivered into the tissues surrounding the eye rather than into the eye per se.

Additionally, despite its apparent advantages, iontophoresis is really just a method of limiting the invasiveness of drug delivery into the eye's interior. Once inside the eye, the pharmacokinetics of water soluble compounds are identical to those following intravitreal injections i.e. their half-lives are on the order of a few hours. Therefore, in many cases, traditional iontophoresis must be repeated as frequently as intravitreal injections, leading to patient inconvenience, increased costs, and increased possibility of untoward effects caused by the iontophoretic treatment itself.

The problem of patient compliance may be compounded by the need to receive daily treatment in a medical facility with high healthcare costs and limited resources and practitioners for treating retinal diseases. Existing ocular iontophoresis systems are not patient-friendly, require multiple parts and assembly to practice, and include clumsy and/or complicated procedures. As such, they require the involvement of experienced healthcare professionals to perform the treatments. Paraprofessional and/or in-home self administration use of such devices are precluded by the technical complexity of many existing iontophoretic devices, as well as the costs of expensive dose-controlling equipment. Individuals have a greater tendency to deviate from a medication regimen when required to leave home for medical treatment, particularly when such treatment is frequent.

SUMMARY OF THE INVENTION

Accordingly, the present invention provides methods and devices for non-invasively delivering an active agent to the eye of a subject. In one aspect, for example, a device for delivering an active agent to an eye of a subject may include an ocular lens-shaped housing configured to contact a surface of the eye, and a reservoir coupled to the housing and configured to deliver an active agent to the eye, wherein the reservoir is located entirely within a 180 degree section of the housing. In another aspect, the reservoir is located entirely within a 150 degree section of the housing.

A variety of mechanisms are contemplated to deliver an active agent from the reservoir and into the eye. For example, in one aspect the active agent may be delivered by passive mechanisms. In another aspect, the reservoir may further include an electrode configured to provide an electrical current capable of iontophoresing an active agent.

Additional elements may be included in the device for enhancing delivery of the active agent. For example, in one aspect a vacuum port may be coupled to the housing and configured to create negative pressure between the housing and the surface of the eye. One specific example of such a vacuum port may include a vacuum bulb. Furthermore, the housing of the device may be configured in size and shape to allow the subject's eyelids to close substantially thereover when positioned on the eye.

The reservoir may be configured in a variety of ways, depending on the overall design and intended functionality of the device. For example, in one aspect the reservoir may be a plurality of reservoirs located entirely within a 180 degree section of the housing. Numerous configurations for a plurality of reservoirs are contemplated. For example, in one specific aspect the plurality of reservoirs may be configured in a side-by-side arrangement. In another aspect, the plurality of reservoirs may be configured in a nested arrangement with respect to the center of the housing.

Various configurations for the lens-shaped housing are also contemplated. In one aspect, for example, the housing may be configured as a corneal lens. In another aspect, the housing may be configured as a scleral lens. In yet another aspect, a portion of the housing may be configured to extended into a cul-de-sac under an eyelid of the eye of the subject such that electrical current flow is hindered between the eye and the eyelid. In a further aspect, the housing may be configured to position the reservoir in a lower cul-de-sac of the eye.

The present invention additionally provides methods for ocularly delivering an active agent into the eye of a subject. For example, in one aspect a method for a method for enhancing ocular delivery of an active agent to the eye of a subject may include contacting an ocular lens-shaped housing having a reservoir containing the active agent against an eye surface such that the reservoir contacts a delivery region of the eye, wherein said reservoir is located entirely within a 180 degree section of the housing, and delivering the active agent from the reservoir into the eye while substantially maintaining alignment between the reservoir and the delivery region. In another aspect, substantially maintaining alignment may further include applying a vacuum between the housing and the eye surface sufficient to maintain the reservoir substantially in alignment with the delivery region during delivery of the active agent.

The delivery of the active agent from the reservoir and into the eye may be by a variety of passive or active mechanisms. For example, in one aspect the active agent is delivered from the reservoir into the eye by an active mechanism such as iontophoresis. In another aspect, the active agent is delivered from the reservoir into the eye by a passive mechanism such as passive diffusion.

In yet another aspect of the present invention, a method is provided for iontophoretically delivering an active agent to an eye of a subject. Such a method may include positioning a device according to aspects of the present invention on the surface of the eye of the subject, and activating the device to deliver the active agent into the eye. Additionally, in another aspect positioning the device further includes applying negative pressure between the device and the eye.

In a further aspect of the present invention, a device for delivering an active agent to an eye of a subject is provided. Such a device may include an ocular lens-shaped housing configured to contact a surface of the eye, and a reservoir coupled to the housing and configured to deliver an active agent to the eye, wherein the reservoir surface area configured to face the eye is less than about 50% of the surface area of the housing configured to face the eye. Additionally, in one aspect the reservoir may be a plurality of reservoirs. In another aspect, each of the plurality of reservoirs has a surface area configured to face the eye that is less than about 50% of the surface area of the housing configured to face the eye. In a further aspect, the plurality of reservoirs is a plurality of annular reservoirs.

A variety of exemplary techniques are contemplated for maintaining the alignment between the reservoir contact surface and the delivery region. In one aspect, substantially maintaining alignment may further include applying a vacuum between the housing and the eye surface sufficient to maintain the reservoir substantially in alignment with the delivery region during delivery of the active agent. In another aspect, substantially maintaining alignment may further include applying a tackifier between the housing and the eye surface sufficient to maintain the reservoir substantially in alignment with the delivery region during delivery of the active agent. In a further aspect, substantially maintaining alignment may be achieved by configuring the shape of the housing such that the housing resists movement in the eye.

The particular active agent to be delivered may be a variety of substances depending on the particular treatment to be effected. Such substances may include drugs in various forms, including prodrugs thereof, and sustained release formulations, as required in order to provide convenient and effective non-invasive delivery. Exemplary active agents are enumerated further herein.

DETAILED DESCRIPTION OF THE INVENTION

Before the present systems and methods for ocular drug delivery are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It must be noted that, as used in this specification and the appended claims, the singular forms "a," "an," and, "the" include plural referents unless the context clearly dictates otherwise. Thus, for example, reference to "a polymer" includes reference to one or more of such polymers, and "an excipient" includes reference to one or more of such excipients.

Definitions

In describing and claiming the present invention, the following terminology will be used in accordance with the definitions set forth below.

As used herein, "formulation" and "composition" may be used interchangeably herein, and refer to a combination of two or more elements, or substances. In some embodiments a composition may include an active agent, an excipient, or a carrier to enhance delivery, depot formation, etc.

As used herein, "active agent," "bioactive agent," "pharmaceutically active agent," and "pharmaceutical," may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical, and medicinal arts. Examples of drugs useful in the present invention include without limitation, steroids, antibacterials, antivirals, antifungals, antiprotozoals, antimetabolites, immunosuppressive agents, VEGF inhibitors, ICAM inhibitors, antibodies, protein kinase C inhibitors, chemotherapeutic agents, neuroprotective agents, nucleic acid derivatives, aptamers, proteins, enzymes, peptides, and polypeptides.

As used herein "prodrug" refers to a molecule that will convert into a drug (its commonly known pharmacological active form). Prodrugs themselves can also be pharmacologically active, and therefore are also expressly included within the definition of an "active agent" as recited above. For example, dexamethasone phosphate can be classified as a prodrug of dexamethasone, and triamcinolone acetonide phosphate can be classified as a prodrug of triamcinolone acetonide.

As used herein, "tackifier" refers to a substance that increases the adherence of an ocular lens device to an eye surface as compared to the ocular device in the absence of a tackifier.

As used herein, "effective amount," and "sufficient amount" may be used interchangeably and refer to an amount of an ingredient which, when included in a composition, is sufficient to achieve an intended compositional or physiological effect. Thus, a "therapeutically effective amount" refers to a non-toxic, but sufficient, amount of an active agent to achieve therapeutic results in treating a condition for which the active agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics,* Vol. 8 (1986), incorporated herein by reference.

As used herein, "sclera" refers to the sclera tissue in the eye or the conjunctiva between the limbus and the formix on the surface of the eye, which is the white part of the eye. "Sclera" is also used in referring to other eye tissues.

As used herein, "subject" refers to a mammal that may benefit from the administration of a composition or method as recited herein. Examples of subjects include humans, and may also include other animals such as horses, pigs, cattle, dogs, cats, rabbits, aquatic mammals, etc.

As used herein, "noninvasive" refers to a form of administration that does not rupture or puncture a biological membrane or structure with a mechanical means across which a drug or compound of interest is being delivered. A number of noninvasive delivery mechanisms are well recognized in the transdermal arts such as patches, and topical formulations. Many of such formulations may employ a chemical penetration enhancer in order to facilitate non-invasive delivery of the active agent. Additionally, other systems or devices that utilize a non-chemical mechanism for enhancing drug penetration, such as iontophoretic devices are also known. "Minimally invasive" refers to a form of administration that punctures a biological membrane or structure but does not cause excessive discomfort to the subjects and severe adverse effects. Examples of "minimally invasive" drug delivery are microneedle, laser, or heat punctuation in transdermal delivery and periocular injections in ocular delivery.

As used herein, "depot" refers to a temporary mass inside a biological tissue or system, which includes a drug that is released from the mass over a period of time. In some aspects, a depot may be formed by the interaction of an active agent with a depot forming agent, such as a complexing ion which will form an active agent complex that is less soluble than the active agent by itself, and thus precipitate in-vivo.

As used herein, the term "reservoir" and refer to a body or a mass that may contain an active agent, a depot forming agent, or other pharmaceutically useful compound or composition. As such, a reservoir may include any structure that may contain a liquid, a gelatin, a semi-solid, a solid or any other form of active agent or secondary compound known to one of ordinary skill in the art. In some cases, an electrode may be considered to be a reservoir. The reservoir may be made of a number of suitable materials. However, in one aspect, such a material may be an electrically non-conductive, or semi-conductive material. In yet another aspect, the reservoir may also include a barrier element configured to attach at a distal portion of the reservoir housing and therefore rest between the reservoir housing and the skin surface or tissue of a subject when the reservoir assembly is in use. Such barrier element can be made of an electrically non-conductive material, and in some aspects, such material will be different from the material of the lens housing. Examples of such materials include without limitation, polymeric materials, such as adhesives or resins, rubbers, etc. In some aspects it is intended that a reservoir deliver an active agent through passive diffusion. In other aspects a reservoir may include an electrode configured to introduce an electrical current into the reservoir, and thus deliver an active agent actively, functioning as either an anode or a cathode.

As used herein, the terms "anode" and "cathode" refer to the electrical polarity of an electrode. The terms "anode" and "cathode" are well known in the art. It should be noted, however, that in some aspects these descriptive terms may be transitory. When using alternating current, for example, two electrodes will alternate between anode and cathode as the current alternates in electrical polarity.

As used herein, the term "corneal lens" refers to a lens sized to fit approximately over the cornea of the eye.

As used herein, the term "scleral lens" refers to a lens sized to cover and extend beyond the cornea across at least a portion of the sclera of the eye.

As used herein, the term "active electrode" refers to an electrode utilized to iontophoretically deliver an active agent.

As used herein, the term "passive electrode" refers to an electrode that is used to complete an electrical circuit without delivering a compound or substance to a subject.

As used herein, the term "return electrode" refers to an electrode utilized to complete an electrical circuit for active electrode. In one aspect, a return electrode may be an active electrode used to deliver a secondary compound, such as an active agent, a depot forming agent, etc. In another aspect, a return electrode may be a passive electrode.

As used herein, the term "self-contained" refers to a device that contains therein, or substantially therein, all the components required for use. For example, a self-contained iontophoretic device may contain active agents, reservoirs, electrodes, power supplies, etc., within a single housing.

As used herein, the term "reacting" refers to any force, change in environmental conditions, presence or encounter of other chemical agent, etc. that alters the active agent. For example, "reacting" between the active agent and the depot forming agent can be physical or chemical interactions.

As used herein, the term "precipitate" refers to anything less than fully solubilized. As such, a precipitate can include not only crystals, but also gels, semi-solids, increased molecular weight, etc.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value. Furthermore, such an interpretation should apply regardless of the breadth of the range or the characteristics being described.

The Invention

The present invention provides devices and associated methods for delivering an active agent into the eye of a subject. In many circumstances, it is desirable to deliver an active agent through a relatively small area tissue on the surface of the eye in order to more effectively target a specific ocular tissue. In this case, the delivery region on the periphery of the eye through which drug is delivered is established by the contact surface area of a reservoir containing the active agent. Thus there is a spatial correspondence between the reservoir and the delivery region of the eye. When this delivery region of the eye is small, it may be difficult to maintain this spatial correspondence with the reservoir, particularly for delivery devices that are large, bulky, and/or handheld. In such cases, movements by the subject and/or the individual holding the device may cause spatial misalignment between the delivery region and the reservoir. Such a misalignment may affect the efficiency of delivery of the active agent. For example, in many cases tissues through which an active agent has been passing may be "primed" and thus may more readily pass additional active agent as compared to tissue that has not been so primed. If the reservoir is shifted because of movement to a non-primed area, the efficiency of active agent delivery may, at least temporarily, decease. In another example, the location of the delivery area on the surface of the eye may be facilitating formation of a drug depot within deeper ocular tissues at a specific location. If the reservoir is shifted in this case, a second drug depot may be formed in a region distinct from the first drug depot. Accordingly, active agent may be more quickly released from two drug depots having an increased surface area as compared to one more concentrated depot, thus reducing the effectiveness of this sustained release mechanism.

It has thus been discovered that administration of an active agent into the eye of a subject can be improved or maximized by maintaining a spatial correspondence between the reservoir delivering an active agent and the tissue region through which the agent is passing. In one aspect, such a spatial correspondence may be maintained by reducing the size and bulkiness of the delivery device. In another aspect, the spatial correspondence may be maintained by increasing the adherence of the delivery device to the surface of the eye to minimize movement thereof. It should be noted, however, that any technique of maintaining such a spatial correspondence is considered to be within the scope of the present invention.

Accordingly, in one aspect a method for enhancing ocular delivery of an active agent to the eye of a subject is provided. Such a method may include contacting an ocular lens-shaped housing having a reservoir containing the active agent against an eye surface such that the reservoir contacts a delivery region of the eye, wherein said reservoir is located entirely within a 180 degree section of the housing. The method may also include delivering the active agent from the reservoir into the eye while substantially maintaining alignment between the reservoir and the delivery region.

The reservoir surface area facing the eye may be understood to be the proportion of the surface area of an ocular lens housing associated with the reservoir through which an active agent is capable of passing, as compared to the total surface area of the ocular lens that is contacting or is facing and in close proximity with the surface of the eye. In the case of multiple reservoir assemblies in a single ocular lens device, the area of contact for the reservoir would include the combined surface area of all of the reservoir assemblies. As has been described, in one aspect the reservoir surface area may be less than or equal to about 50% of lens area facing the eye. In another aspect, the reservoir surface area may be less than or equal to about 25% of lens area facing the eye. In yet another aspect, the reservoir surface area is less than or equal to about 10% of lens area facing the eye.

In addition to surface area, in one aspect the reservoir is located entirely within a 180 degree section of the lens housing. In another aspect, the aspect the reservoir is located entirely within a 150 degree section of the lens housing. In those aspects including a plurality of reservoirs, all reservoirs are located within the same 180 degree section of the device. In some aspects the plurality of reservoirs are arranged in a side-by-side configuration. In other aspect, the plurality of reservoirs may be arranged in a nested pattern with respect to the center of the housing.

A variety of techniques are contemplated for maintaining the alignment between the reservoir and the delivery region. As has been described, maintaining such an alignment may facilitate more effective delivery of an active agent into deeper ocular tissues. In one aspect, for example, alignment may be maintained due to the shape configuration of the lens housing. For example, a scleral lens has a somewhat oval shape to match the shape of the eye. This somewhat oval shape helps to prevent rotation of the housing in the eye. Additionally, because the curvature of an ocular lens-shaped housing closely matches the curvature of the eye, capillary forces between the housing and the eye may cause greater adhesion therebetween as compared to a housing with a mismatched shape.

Figure 1:
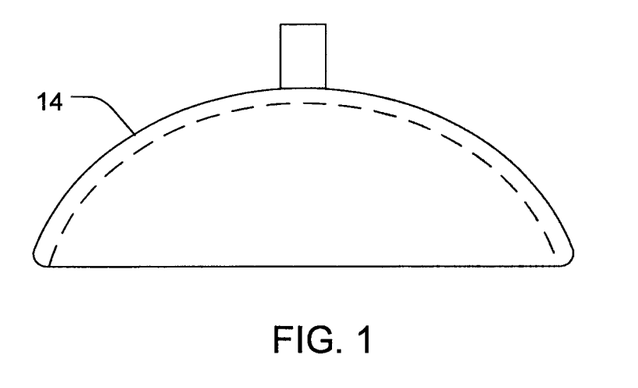
FIG. 1 is a side view of a scleral lens device in accordance with an aspect of the present invention.
Figure 2:
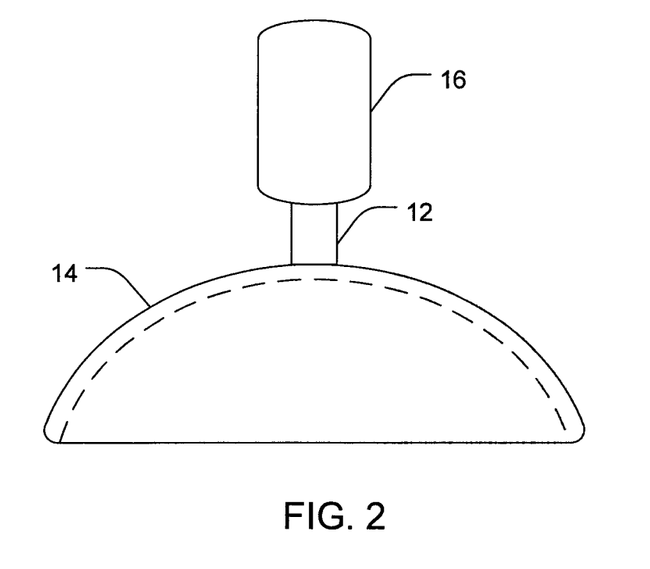
FIG. 2 is a side view of a scleral lens device in accordance with another aspect of the present invention.

Additionally, maintaining the alignment between the reservoir and the delivery region may be further enhanced by applying a vacuum between the lens device and the eye surface sufficient to maintain the reservoir contact surface area substantially in alignment with the delivery region during delivery of the active agent. Such a suction mechanism may even hold the device in place during blinking in some aspects. Following delivery of the active agent, the device can be pressurized at the interface surface between the eye and the lens device to allow release and subsequent removal. The vacuum may be applied by any technique known to one of ordinary skill in the art. In one aspect, as is shown in FIG. 1, a vacuum port 12 may be incorporated into an ocular lens device 14 to allow attachment of external device to draw the vacuum. Such an external device may include a variety of devices, including pumps, syringes, etc. In another aspect, as is shown in FIG. 2, a vacuum bulb 16 may be coupled to an ocular lens device 14. The vacuum bulb 16 is operated by squeezing the bulb prior to positioning the ocular device 14 on the eye of a subject, and releasing the bulb following such positioning to provide a vacuum between the ocular device 14 and the eye of the subject. In one aspect, the vacuum bulb 16 is coupled to the ocular device 14 by an intermediate structure such as a vacuum port 12. In another aspect, the vacuum port 16 may be coupled directly to the ocular device 14 (not shown). In another aspect, the vacuum may be accomplished by the shape of the device housing alone. For example, a device housing conforming to the surface of the eye may be depressurized by merely applying pressure to the device. Removal of such a device may, however, be more problematic that a device having a means to control pressurization, such as a valve element.

In another aspect, maintaining alignment between the reservoir and the delivery region may be accomplished by applying a tackifier between the lens device and the eye surface sufficient to maintain the reservoir assembly substantially in alignment with the delivery region during delivery of the active agent. A tackifier should be chosen to allow the ocular lens device to be held in place during delivery of the active agent, and to be easily removed following such delivery. Non-limiting examples of tackifiers may include waxes, petroleum jellies, impermeable polymeric or resinous materials, oils, etc.

Though numerous conditions would benefit from the methods and devices of the present invention, they are particularly well suited for the treatment of ocular diseases such as direct, combinatory, and adjunctive therapies. This is because of the relatively high permeability of the eye tissues and the large aqueous compartments in the eye. Examples of eye diseases include without limitation, macular edema, age related macular degeneration, anterior, intermediate, and posterior uveitis, HSV retinitis, diabetic retinopathy, bacterial, fungal, or viral endophthalmitis, eye cancers, glioblastomas, glaucoma, and glaucomatous degradation of the optic nerve.

Accordingly, a wide range of active agents may be used in the present invention as will be recognized by those of ordinary skill in the art. In fact, any agent that may be beneficial to a subject when administered ocularly may be used. Examples of the active agents that may be used in the treatment of various conditions include, without limitation, analeptic agents, analgesic agents, anesthetic agents, antiasthmatic agents, antiarthritic agents, anticancer agents, anticholinergic agents, anticonvulsant agents, antidepressant agents, antidiabetic agents, antidiarrheal agents, antiemetic agents, antihelminthic agents, antihistamines, antihyperlipidemic agents, antihypertensive agents, anti-infective agents, antiinflammatory agents, antimigraine agents, antineoplastic agents, antiparkinsonism drugs, antipruritic agents, antipsychotic agents, antipyretic agents, antispasmodic agents, antitubercular agents, antiulcer agents, antiviral agents, anxiolytic agents, appetite suppressants, attention deficit disorder and attention deficit hyperactivity disorder drugs, cardiovascular agents including calcium channel blockers, antianginal agents, central nervous system ("CNS") agents, beta-blockers and antiarrhythmic agents, central nervous system stimulants, diuretics, genetic materials, hormonolytics, hypnotics, hypoglycemic agents, immunosuppressive agents, muscle relaxants, narcotic antagonists, nicotine, nutritional agents, parasympatholytics, peptide drugs, psychostimulants, sedatives, steroids, smoking cessation agents, sympathomimetics, tranquilizers, vasodilators, β-agonists, and tocolytic agents, and mixtures thereof.

Additionally, further examples of active agents may include steroids, aminosteroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides and mixtures thereof. Specific examples of useful antiviral active agents include acyclovir or derivatives thereof.

Specific examples of active agents may also include hydromorphone, dexamethasone phosphate, amikacin, oligonucleotides, $F_{ab}$ peptides, PEG-oligonucleotides, salicylate, tropicamide, methotrexate, 5-fluorouracil, squalamine, triamcinolone acetonide, diclofenac, combretastatin A4, mycophenolate mofetil, mycophenolic acid, and mixtures thereof.

Under a number of circumstances, the active agent used may be a prodrug, or in prodrug form. Prodrugs for nearly any desired active agent will be readily recognized by those of ordinary skill in the art. Additionally, prodrugs with high electromobility which metabolize into drugs with a low aqueous solubility may be beneficial. In this case, an electrically mobile prodrug of a low solubility drug in iontophoresis can be used to create a sustained release system in the eye. Because the prodrug has high electromobility, it is effectively delivered into the eye. The prodrug then converts into the low solubility drug in the eye and the insoluble drug precipitates in the eye. The drug in solid state in the eye will be slowly released into the eye and provide an ocular sustained release condition.

Though any prodrug would be considered to be within the scope of the present invention, examples may include the derivatives of steroids, antibacterials, antivirals, antifungals, antiprotozoals, antimetabolites, VEGF inhibitors, ICAM inhibitors, antibodies, protein kinase C inhibitors, chemotherapeutic agents, immunosuppressive agents, neuroprotective agents, analgesic agents, nucleic acid derivatives, aptamers, proteins, enzymes, peptides, polypeptides, and mixtures thereof. One specific example of a steroid derivative may include triamcinolone acetonide phosphate or other derivatives of triamcinolone acetonide, dexamethasone phosphate, etc. For example, it may be preferable to label a steroid with one or more phosphate, sulfate, or carbonate functional groups, so the prodrug can be effectively delivered into the eye and form a complex with the precipitating ion.

Active agents may be delivered by a variety of mechanisms into an eye of the subject. In one aspect, for example, the active agent may be iontophoretically administered. In such a case, an electrical current delivered from an electrode is utilized to drive the active agent from the reservoir and into the eye. Such an active delivery mechanism is used to drive an active agent having a charge of the same polarity as the electrical current into the eye. Iontophoretic techniques are well known in the art, and any such technique should be considered to be within the scope of the present invention.

In one aspect, an ocular iontophoretic device may include at least two electrodes having opposite charge characteristics, such as an anode and a cathode. Depending on the configuration of the ocular device, both electrodes may be placed on the eye surface, or one electrode may be placed on the eye surface and the other may be located remote from the eye in a location such as an earlobe. The anode and cathode are intended to pass current due to a potential difference established therebetween by a power source. The current acts to move an active agent iontophoretically in a direction that is dependent on the charge characteristics of the active agent and the charge orientation of the potential difference between the anode and the cathode. An active electrode, whether it is an anode or a cathode, is designed to deliver electrical current across an associated reservoir to iontophoretically deliver the active agent located therein. In one aspect, one electrode may be an active electrode and the other electrode may be a return electrode for merely completing the electrical circuit. For example, the active electrode may be an anode and the return electrode may be a cathode, or vice versa. In another aspect, one both the anode and the cathode may each have an associated reservoir for the delivery of compounds, as is described more fully herein. The compounds may be the same or different, depending on the intended use and/or configuration of the device. The anode and the cathode can be of the same or different size relative to each other. Also, the surface area of one or both electrodes can be configured to modify their respective current densities when in use.

The anode and cathode can be of any material or manufacture known to one skilled in the art. Various examples include metal electrodes, conductive glass electrodes, conductive fluids or gels, etc. A single electrode may be coupled to a single reservoir or to multiple reservoirs depending on the particular configuration of a given reservoir assembly. Conversely, multiple electrodes having the same polarity may be coupled to a single reservoir in certain aspects.

As has been described, in some aspects a return electrode is located remote from the eye. Such configurations are inconvenient and allow various conductive pathways to be formed across the tissues surrounding the eye rather than focused only in the eye per se. Placing both the anode assembly and the cathode assembly on the surface of the eye may facilitate the passage of electrical current transsclerally into the eye under the anode and cathode, particularly when current movement across the surface of the eye is limited. In one aspect, the anode assembly and the cathode assembly may be respectively configured on the surface of the eye such that the anode and the cathode complete an electrical circuit substantially within the eye of the subject. In other words, the current between the anode and the cathode may pass predominantly through the eye tissues rather than into or through the connective tissues surrounding the eye. In one aspect, both the anode and the cathode may be oriented within the anode and cathode assemblies to face the surface of the eye. The anode and the cathode may directly contact the surface of the eye, or they may contact the surface of the eye through an intermediate material or reservoir that is part of the device. In either case, such a "direct" contact between the electrodes and the eye surface may facilitate the focusing of electrical current within the eye.

The relative spacing or the inter-electrode distance between the anode and the cathode may play an important role in determining where an active agent is localized in the eye upon delivery. As such, in accordance with one aspect of the present invention, the anode and the cathode may be spaced at an inter-electrode distance which controls the depth and extent of penetration of the active agent within the eye. Such a spacing may focus the electric field more effectively within the eye, thus more effectively delivering the active agent. Increasing the inter-electrode distance will generally cause current to flow deeper into the eye, thus iontophoretically delivering the active agent deeper. Small inter-electrode distances will cause a more superficial delivery of active agent into the eye. Thus, by altering the physical locations of each of the electrode assemblies, and thus the inter-electrode distance between them, the active agent can be delivered to particular regions of the eye at specific depths. As such, the inter-electrode distance may vary depending on the intended delivery location. In one aspect of the present invention, however, the inter-electrode distance may be less than about 40.0 mm. In yet another aspect, the inter-electrode distance may be from about 1 mm to about 10 mm. In a further aspect, the inter-electrode distance may be from about 0.3 mm to about 4 mm.

In another aspect of the present invention, devices utilizing iontophoretic delivery mechanisms may include an electrically insulating barrier located between the anode and the cathode to preclude or reduce electrical current flow across the surface of the eye. By preventing current flow across the eye surface between the anode and the cathode, current is focused, or forced transsclerally into the eye to complete an electrical circuit. In one aspect, the barrier element located on the device between the anode and the cathode and configured to contact the surface of the eye. As such, the barrier element is configured to electrically isolate the anode from the cathode at the surface of the eye. In another aspect, the barrier element may surround each of the anode assembly and the cathode assembly at the surface of the eye to preclude the passage of fluid and minimize current flow between the anode and the cathode. The barrier element may be constructed of any electrically inert material known that is capable of forming a barrier. The barrier element material may be the same material as the reservoir and/or the device housing, or it may be a different material selected for its dielectric properties. The barrier element may also be physically coupled to the reservoir assembly, or it may be a protruding portion of the device housing, and thus be continuous with the housing or reservoir. In those aspects where the barrier element is not continuous with the housing or reservoir, the barrier element may be comprised of a material that is either the same or different from either the device housing or the reservoir material. Non-limiting examples of barrier element materials may include plastics, composites, nylons, polyesters, polyurethanes, polyethylenes, polycarbonates, etc. Barrier element materials may also include conductive materials such as metals provided the material is rendered non-conductive by coating or other means.

The power sources of the present invention may be any component known to one of ordinary skill in the art that is capable of powering an iontophoretic device. Powering the iontophoretic device includes providing an electrical current or an electrical potential facilitating the delivery of an active agent. In those aspects having power sources self-contained within the device housing, it may be beneficial for the power source to be a flexible battery or the like. Conductive subcomponents may be utilized to electrically couple the power source to the anode and to the cathode. These conductive subcomponents may include wires, traces, microelectronics, or other conductive materials such as conductive fluids within insulated tubing or channels. Such microelectronics may be useful in controlling the delivery of the active agent, and/or for safety purposes.

The reservoirs according to aspects of the present invention are designed to hold an active agent or other secondary substance to be delivered prior to administration through the eye tissues of a subject. Reservoirs may be configured to passively or actively deliver an active agent into the eye. Active reservoirs, for example, are configured to receive electrical current from an electrode to thus iontophoretically deliver an active agent or other compound therefrom. In one aspect, a reservoir may be a distinct compartment, having a lumen for holding an active agent or other secondary compound to be delivered. Additionally, such a reservoir may contain at least one access port to allow the reservoir to be filled while in contact with the body surface of the subject. This configuration may allow the reservoir to be filled during use as the agent within is depleted. In another aspect, a reservoir may be filled during manufacture of the device with an active agent or other secondary compound to be delivered, particularly in those aspects where the device is intended for a single use. Various iontophoretic reservoir materials are known to those skilled in the art, and all are considered to be within the scope of the present invention. Additionally, the active agent or secondary substance may be included in the reservoir in any form, including, without limitation, a liquid, gelatinous, semi-solid, or solid form. In another aspect the reservoir may consist of a portion of the active electrode, such that an active agent or secondary substance is delivered from the electrode when electrical current is introduced.

For optimal iontophoretic delivery of active agents and other compounds into the eye, a permselective material may be placed in ion-conducting relation to the eye surface. An electric current of AC, DC, and AC with superimposed DC can be used to transport the compound of interest through the permselective material into the eye. The permselective material is capable of hindering iontophoretic transport of a competing ion and thus may increase the transference efficiency of the active agent or other compound of interest during iontophoresis. As a result, the active agent may be delivered iontophoretically into the eye more efficiently than iontophoresis without the permselective material. For example, more efficient iontophoretic transport can be achieved by placing the permselective material against an active electrode (e.g., Ag/AgCl) between the electrode and a reservoir to prevent the products of electrochemical reactions generated at the electrode surface (e.g., Ag or Cl ions) from moving into the reservoir. Another example is to place the permselective material at the interface between the surface of the eye and the device. As such, the permselective material may be located between the eye surface and the reservoir to prevent the migration of the active agent and endogenous ions into a reservoir containing a secondary substance of opposite charge, or vice versa the secondary substance and endogenous ions into the active agent reservoir during iontophoresis. Any permselective material capable of hindering iontophoretic transport of a competing ion during iontophoretic transport of the compound of interest may be used in conjunction with the invention. The permselective material may be provided in any of a number of forms as described in applicant's copending U.S. patent application Ser. No. 10/371,148 entitled "METHODS AND SYSTEMS FOR CONTROLLING AND/OR INCREASING IONTOPHORETIC FLUX", filed on Feb. 21, 2003, which is incorporated herein by reference. For example, the material may be provided in a liquid, partially liquid, gelled, partially solid, or fully solid state. In some instances, the permselective material may be supported by a support structure such as an additional membrane having sufficient porosity and chemical inertness so as to avoid interfering with the performance of the permselective material, yet having sufficient mechanical integrity for ease in handling. The material can also be provided in the form of a membrane having a surface sized and/or shaped for direct contact with the eye or shaped for direct contact with an active electrode (e.g., Ag/AgCl). In other instances, the permselective material may be comprised of a polyelectrolyte, which can be a single molecule or an aggregate of molecules having ions or ionizable groups. Additionally, in one aspect a permselective material may be functionally coupled to an electrode delivering an active agent or secondary compound, and/or to an electrode merely completing the electrical circuit.

In addition to active delivery techniques, aspects of the present invention also provide ocular delivery devices and associated methods that utilize passive techniques to delivery the active agent into the eye. Thus an ocular lens device may be positioned on the eye for a sufficient period of time to allow an active agent located therein to diffuse from the device and into the eye. The various techniques for maintaining alignment between the reservoir surface contact area and the delivery area may thus facilitate the immobilization of the ocular lens device with respect to the eye surface for the longer durations that may be required to passively deliver an active agent to the eye.

It is also contemplated that reservoirs containing additional compounds or substances may be incorporated into both passive and active delivery devices according to aspects of the present invention. In one aspect, for example, a secondary reservoir assembly may be contacted against the eye surface so that the secondary reservoir contacts a secondary delivery region of the eye. A secondary substance may be delivered from the secondary reservoir into the eye while substantially maintaining alignment between the secondary reservoir and the secondary delivery region.

The secondary substance may be delivered in a similar or in a different manner compared to the active agent. For example, in one aspect both the active agent and the secondary substance may be iontophoretically administered. In another aspect, the active agent may be iontophoretically administered and the secondary substance may be passively delivered. In another aspect, the active agent may be passively delivered and the secondary substance may be iontophoretically delivered.

As with the reservoir contact surface area, secondary reservoir surface area facing the eye may be understood to be the proportion of the surface area of an ocular lens housing associated with the secondary reservoir through which a secondary substance is capable of passing, as compared to the total surface area of the ocular lens that is contacting or is facing and in close proximity with the surface of the eye. In the case of multiple secondary reservoirs in a single ocular lens device, the secondary reservoir surface contact area would include the combined surface area of all of the secondary reservoir assemblies. As has been described, in one aspect the secondary reservoir assembly contact surface area is less than or equal to about 50% of lens area contacting the eye. In another aspect, the secondary reservoir assembly contact surface area is less than or equal to about 25% of lens area contacting the eye. In yet another aspect, the secondary reservoir assembly contact surface area is less than or equal to about 10% of lens area contacting the eye.

A variety of secondary substances may be included in a secondary reservoir. For example, in one aspect the secondary substance may include a secondary active agent, a depot forming agent, a vasoconstrictor agent, or a combination thereof. As has been described, a secondary substance may be delivered by an active mechanism such as iontophoresis, or by a passive mechanism such as diffusion.

In some cases, for example, ocular treatment may be hampered by the in-vivo movement/clearance of the active agent in the eye. It is therefore contemplated that various means for restricting or slowing such movement may improve the effectiveness of the active agent therapy. In one aspect, the in-vivo movement may be restricted by constriction of the blood vessels exiting an area in which the active agent is being delivered or precipitated. Such constriction may be induced by the administration of a secondary substance such as a vasoconstricting agent. Such a vasoconstrictor may be administered actively by iontophoretic or other means, or it may be delivered passively. Specific non-limiting examples of vasoconstricting agents may include α-agonists such as naphazoline, and tetrahydrozoline, sympathomimetics such as phenylethylamine, epinephrine, norepinephrine, dopamine, dobutamine, colterol, ethylnorepinephrine, isoproterenol, isoetharine, metaproterenol, terbutaline, metearaminol, phenylephrine, tyramine, hydroxyamphetamine, ritrodrine, prenalterol, methoxyamine, albuterol, amphetamine, methamphetamine, benzphetamine, ephedrine, phenylpropanolamine, methentermine, oxymetazoline, phentermine, fenfluramine, propylhexedrine, diethylpropion, phenmetrazine, and phendimetrazine. In one specific aspect, the vasoconstricting agent is oxymetazoline. Vasocontricting agents can be administered either before or concurrently with the administration of the active agent. Though administration of the vasoconstrictor may occur following administration of the active agent, the results may be less effective than prior or concurrent administration. Additionally, in some aspects, the vasoconstricting agent may have the same polarity as the active agent and administered concurrently with the active agent. Similarly, the vasoconstricting agent may have the opposite polarity as active agent, and thus be administered from a return electrode assembly.

Various treatment regimens according to aspects of the present invention are contemplated. In one aspect, the administered active agent may provide an immediate therapeutic effect. In another aspect, the active agent may provide a sustained therapeutic effect. In yet another aspect, the active agent may provide an immediate therapeutic effect and a sustained therapeutic effect. In many cases, some form of sustained release may be beneficial in order to reduce the frequency of administration. Such a reduction in administration may increase patient compliance and reduce the frequency of eye infections and other related issues due to the decreased physical contact with the eye.

Various methods of providing sustained release, and therefore sustained therapeutic effect, are contemplated, some of which have been discussed herein. Such a sustained release may be due to a property of the active agent, the use of a prodrug, the use of a sustained release depot, etc. In one aspect, a sustained release depot may be formed in the eye tissue by the reaction of an active agent with a secondary substance such as a depot forming agent following delivery of the active agent to the subject. The depot forming agent may be delivered to the subject as a secondary substance, or it may be an endogenous substance that reacts with the active agent. In either case, the depot forming agent and the active agent do not interact with one another until the active agent is delivered into the subject. As such, in most cases the active agent and the depot forming agent will be separated until both are located in-vivo. If the depot forming agent is to be delivered to the subject, then both agents should be delivered separately. Endogenous depot forming agents will, of course, not come into contact with the active agent until administration occurs. Thus an in-vivo reaction between the active agent and the depot forming agent will cause the active agent or a derivative thereof to form a depot. In one aspect such a depot forming mechanism may be a change in the solubility of the active agent or a derivative of the active agent, thus causing precipitation and subsequent depot formation. This depot of active agent complex is then able to deliver a therapeutic compound to the biological system over time. Such sustained delivery can include local or systemic delivery of the active agent to the subject. As such, in one embodiment, a depot forming agent may be created at a desired location in a subject, and the active agent may be systemically administered and may "collect" at the depot forming agent to form a depot as the active agent circulates through the body. In another aspect, the depot forming agent may not react directly with the active agent, but still functions to facilitate the formation of a sustained release depot. In such a case, the depot forming agent may react with an area of a local environment to cause an alteration therein. The active agent would then react with the altered area of the local environment to form a depot as a result of the changes facilitated by the depot forming agent.

As a sustained release mechanism, it will be recognized that the depot formulation of the present invention generally has an in-vivo solubility that is lower than that of the active agent by itself. In this way, as the active agent dissolves out of the depot over time, a sustained therapeutic effect may be obtained. Further, since the active agent in the depot is unable to have a therapeutic effect until released therefrom, the solubility properties of the depot limit potential toxicity or overdose concerns that would normally arise when delivering a sufficient amount of drug to last over a prolonged period. Further details on such depot administration and depot agents can be found in U.S. patent application Ser. Nos. 11/238,144 and 11/238,104, both filed on Sep. 27, 2005, both of which are incorporated herein by reference.

Figure 3:
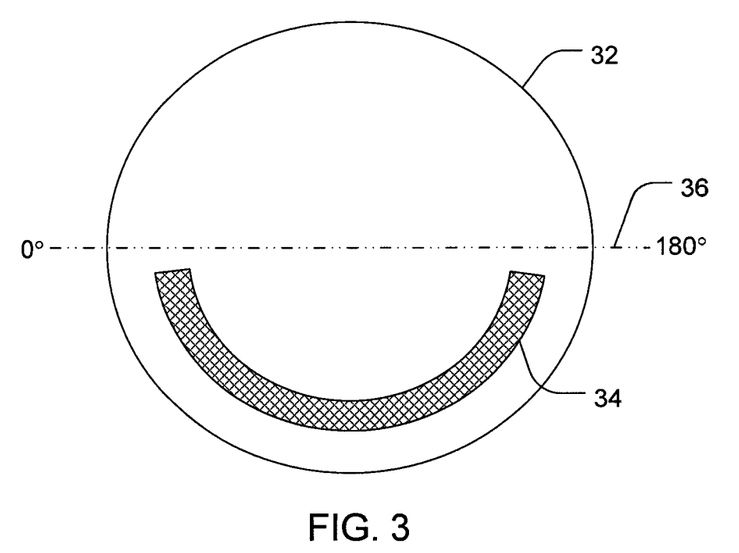
FIG. 3 is a top view of a scleral lens device in accordance with yet another aspect of the present invention.
Figure 4:
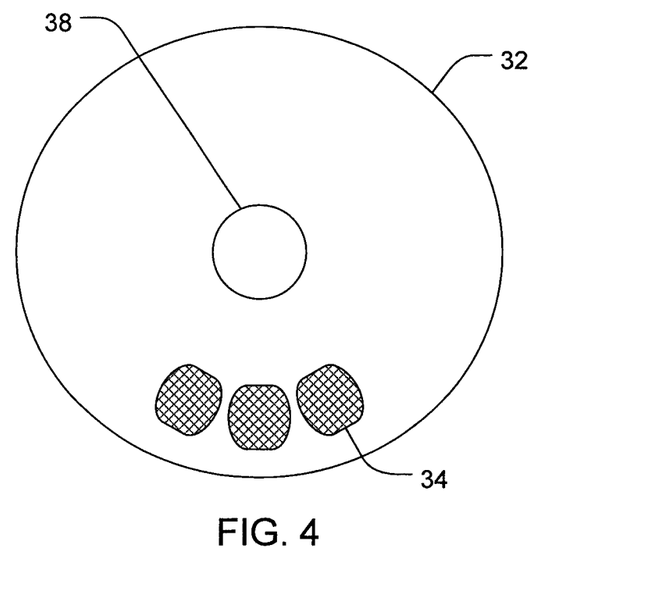
FIG. 4 is a top view of a scleral lens device in accordance with a further aspect of the present invention.

Numerous configurations for the ocular lens devices of the present invention are contemplated, for both single-use and multiple-use devices. FIG. 3, for example, shows an ocular lens-shaped housing 32 having a reservoir 34 configured to contain an active agent. The reservoir 34 is located entirely within a 180° section of the housing 32, as is indicated by 36. FIG. 4 shows one aspect having multiple reservoirs 34 located side-by-side entirely within a 180° section of the housing 32. Additionally, a vacuum port 38 may optionally be coupled to the ocular lens housing 32 in order to generate a vacuum between the device and the surface of the eye during delivery of the active agent. Although FIG. 4 shows three reservoirs 34 in the housing, it should be understood that this is merely exemplary, and any number of such reservoirs can be incorporated into an ocular device. As has been described, in one aspect it is also contemplated that a single reservoir assembly be included in the ocular lens housing.

Figure 5:
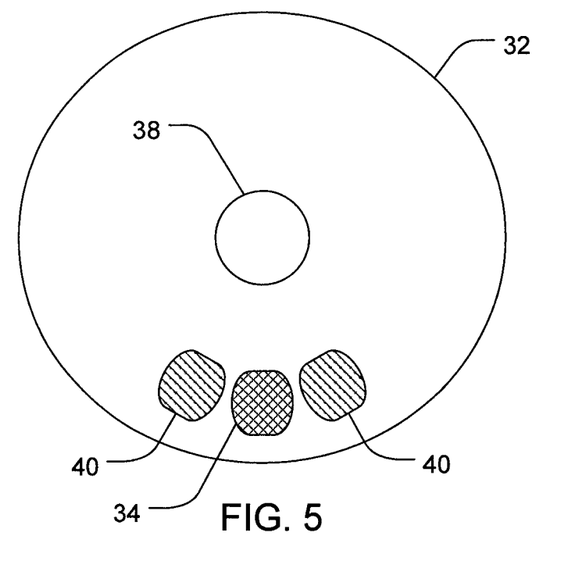
FIG. 5 is a top view of a scleral lens device in accordance with another aspect of the present invention.

FIG. 5 shows one aspect having a housing 32 with a reservoir 34, a vacuum port 38, and two secondary reservoirs 40. The number of secondary reservoirs will vary depending on the configuration of a particular device, and should not be considered as limiting. Additionally, the secondary reservoirs 40 may be located proximal to a reservoir 34 as shown, or they may be positioned at a more distal location.

Figure 6:
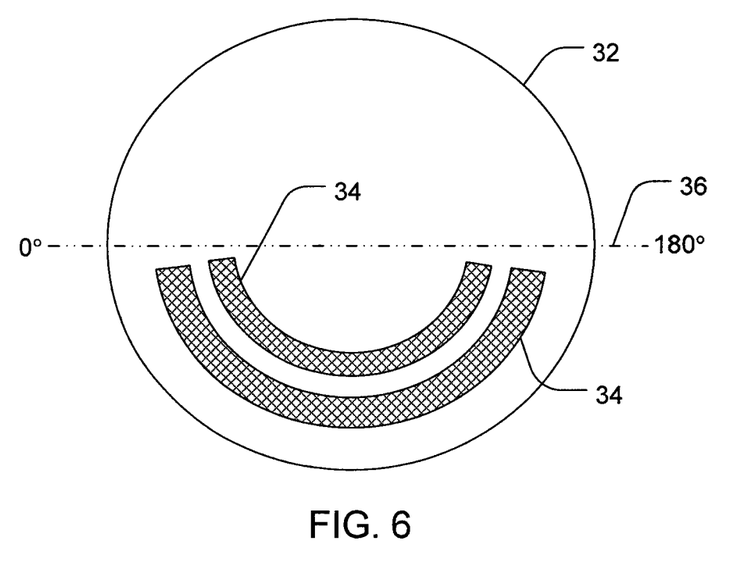
FIG. 6 is a top view of a scleral lens device in accordance with another aspect of the present invention.

FIG. 6 shows one aspect having a housing 32 with two reservoirs 34, where the reservoirs are configured in a nested arrangement with respect to the center of the housing. In this aspect, both of the reservoirs 34 are located entirely within the same 180° section 36 of the housing 32.

It is also contemplated that the ocular lens housing may be of any shape that conforms to fit the surface of the eye. In one aspect, for example, the ocular lens housing may be a corneal lens housing, and thus be shaped to fit at least substantially over the cornea. In another aspect, the ocular lens housing may be a scleral lens housing, and thus be shaped to fit at least substantially over the scleral tissues of the eyes. In such an example, the ocular lens housing would be configured to extended into a cul-de-sac under an eyelid of the eye of the subject. Such a configuration may hinder electrical current flow between the eye and the eyelid. In one aspect, the ocular lens housing may be configured such that the reservoir or reservoirs associated therewith are positioned within the lower cul-de-sac of the eye during use. As the lower eyelid generally exhibits less movement during blinking, such a configuration may assist in maintaining the position of the ocular housing during use.

Various materials are contemplated for use as the ocular lens housing that may securely hold the various components of the device. It may be additionally beneficial to utilize materials that provide some level of flexibility to avoid damage or irritation to the eye surface. Any material having properties beneficial to the construction of such a device would be considered to be within the scope of the present invention. For example, the housing material may include, without limitation, plastics, metals, composites, Teflon, nylons, polyesters, polyurethanes, polyethylenes, polycarbonates, etc. Materials such as metals may be utilized that are conductive, and thus would need have dielectric materials incorporated therein in order to maintain electrical isolation between various components of the device through the housing in those aspects utilizing iontophoretic delivery techniques.

EXAMPLES

Example 1

Figure 7:
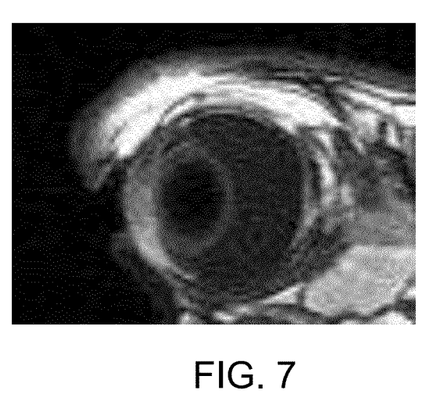
FIG. 7 is an MRI image of a rabbit eye in accordance with yet another aspect of the present invention.

A handheld ocular iontophoretic device is constructed from a plastic tube, wherein one end is shaped to conform to the eye of a rabbit. An electroplated AgAgCl electrode is positioned in one end of the plastic tube and a hydrogel is inserted into the tube so that one side of the hydrogel contacts the electrode, while the opposite side is configured to contact the eye. The hydrogel has been previously loaded with 1.0M $Mn^{++}$. The iontophoretic device is coupled to a power source and placed against the surface of an eye of a rabbit, partially within the cul-de-sac in a dorsal location. A return electrode is attached to the ear of the rabbit, and finger pressure is used to seal the device against the eye. 2 mA of current is applied to the iontophoretic device for 20 minutes to deliver the $Mn^{++}$ from the hydrogel and into the eye. Distribution of the $Mn^{++}$ within the eye of the rabbit is analyzed using a 3 Tesla Siemens MRI system as is shown in FIG. 7. As can be seen in this figure, $Mn^{++}$ ions (white contrast) were delivered primarily to the eyelid and surrounding tissues with relatively little delivery into the eye itself.

Example 2

Figure 8:
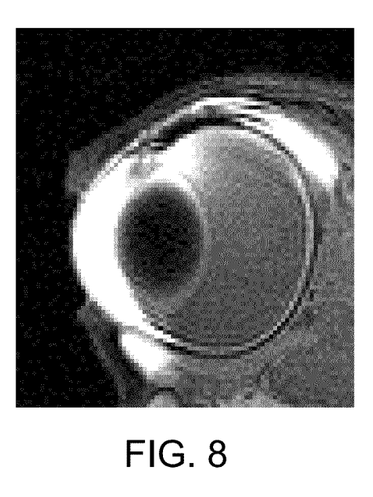
FIG. 8 is an MRI image of a rabbit eye in accordance with a further aspect of the present invention.

An iontophoretic scleral lens device is configured to conform to the eye of a rabbit. An electroplated AgAgCl electrode coupled to a 1.0M $Mn^{++}$ filled hydrogel is located within a reservoir structure along the contact surface of the scleral lens. The iontophoretic device is coupled to a power source and positioned on an eye of a rabbit, such that the reservoir is located partially within the cul-de-sac in a dorsal region of the eye. A return electrode is attached to the ear of the rabbit, and suction is applied to the scleral lens to preclude movement of the lens relative to the eye surface. 3 mA of current is applied to the scleral lens device for 20 minutes to deliver the $Mn^{++}$ from the hydrogel and into the eye. Distribution of the $Mn^{++}$ within the eye of the rabbit is analyzed using a 3 Tesla Siemens MRI system as is shown in FIG. 8. As can be seen in this figure, $Mn^{++}$ ions (white contrast) were delivered primarily into the eye tissues. Additionally, the black region along the dorsal region of the eye represents the formation of a depot of concentrated $Mn^{++}$. Diffusion from this region can be seen in the white band extending toward the posterior eye tissues.

It should be understood that the above-described arrangements are only illustrative of the application of the principles of the present invention. Numerous modifications and alternative arrangements may be devised by those skilled in the art without departing from the spirit and scope of the present invention. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A device for delivering an active agent to an eye of a subject, comprising:
    an ocular lens-shaped housing configured to contact a surface of the eye;
    a plurality of reservoirs coupled to the housing in a side by side arrangement and configured to deliver an active agent to the eye, wherein all reservoirs in the device are located entirely within the same 180 degree section of the housing and are configured in a nested arrangement with respect to a center of the housing; and
    a vacuum port coupled to the housing and configured to create negative pressure between the housing and the surface of the eye.

2. The device of claim 1, wherein the reservoirs are located entirely within a 150 degree section of the housing.

3. The device of claim 1, wherein the reservoirs further include an electrode configured to provide an electrical current capable of iontophoresing the active agent.

4. The device of claim 1, wherein the vacuum port is connected to a vacuum bulb.

5. The device of claim 1, wherein the housing is configured in size and shape to allow the subject's eyelids to close substantially thereover when positioned on the eye.

6. The device of claim 1, wherein a portion of the housing is configured to extend into a cul-de-sac under an eyelid of the eye of the subject such that electrical current flow is hindered between the eye and the eyelid.

7. The device of claim 1, wherein the housing is configured as a corneal lens.

8. The device of claim 1, wherein the housing is configured as a scleral lens.

9. The device of claim 8, wherein the housing is configured to position the reservoirs in a lower cul-de-sac of the eye.

10. A method for enhancing ocular delivery of an active agent to the eye of a subject, comprising:
    contacting a device as recited in claim 1 against an eye surface such that the reservoirs of the device contact a delivery region of the eye; and
    delivering the active agent from the reservoirs of the device into the eye while substantially maintaining alignment between the reservoirs and the delivery region by applying a vacuum between the housing and the eye surface sufficient to maintain the reservoirs substantially in alignment with the delivery region during delivery of the active agent.

11. The method of claim 10, wherein delivering the active agent from the reservoirs further includes actively delivering the active agent.

12. The method of claim 11, wherein actively delivering the active agent from the reservoirs further includes iontophoretically delivering the active agent.

13. The method of claim 10, wherein delivering the active agent from the reservoirs further includes passively delivering the active agent.

14. A method of iontophoretically delivering an active agent to an eye of a subject, comprising:
    positioning the device of claim 1 on the surface of the eye of the subject;
    applying negative pressure between the device and the eye; and
    activating the device to deliver the active agent into the eye.

* * * * *